United States Patent
Gupta (10) Patent No.: US 9,828,629 B2
(45) Date of Patent: Nov. 28, 2017

(54) NUCLEIC ACID TARGET IDENTIFICATION BY STRUCTURE BASED PROBE CLEAVAGE

(71) Applicant: Roche Molecular Systems, Inc., Pleasanton, CA (US)

(72) Inventor: Amar Gupta, Danville, CA (US)

(73) Assignee: Roche Molecular Systems, Inc., Pleasanton, CA (US)

(*) Notice: Subject to any disclaimer, the term of this patent is extended or adjusted under 35 U.S.C. 154(b) by 470 days.

(21) Appl. No.: 14/203,164

(22) Filed: Mar. 10, 2014

(65) Prior Publication Data

US 2014/0272955 A1    Sep. 18, 2014

Related U.S. Application Data

(60) Provisional application No. 61/799,127, filed on Mar. 15, 2013.

(51) Int. Cl.
*C12Q 1/68*    (2006.01)

(52) U.S. Cl.
CPC .......... *C12Q 1/686* (2013.01); *C12Q 1/6823* (2013.01); *C12Q 1/6844* (2013.01)

(58) Field of Classification Search
None
See application file for complete search history.

(56) References Cited

U.S. PATENT DOCUMENTS

| 6,140,053 A * | 10/2000 | Koster ............... C07H 21/00 422/68.1 |
| 7,902,345 B2 | 3/2011 | Van Den Boom et al. |
| 2005/0053939 A1 | 3/2005 | Chenna et al. |
| 2009/0263813 A1 | 10/2009 | Gelfand et al. |
| 2011/0160093 A1* | 6/2011 | Van Den Boom ... C12Q 1/6827 506/16 |

OTHER PUBLICATIONS

Beer, B. et al., "A novel amplification strategy for genotyping with liquid chromatography-electrospray ionization mass spectrometry." Analyst, 2012, 137, p. 5325-5333.

* cited by examiner

*Primary Examiner* — Prabha Chunduru
(74) *Attorney, Agent, or Firm* — Roche Molecular Systems, Inc.

(57) ABSTRACT

The present invention provides for novel methods and compositions for nucleic acid sequence detection. Unique, identifying cleavage fragments from probes, bound to target nucleic acids, are produced during PCR by the 5'-nuclease activity of the polymerase. The identity of the targets can be determined by identifying the unique cleavage fragments.

12 Claims, 5 Drawing Sheets

SEQUENCE LISTING

```
<160> NUMBER OF SEQ ID NOS: 6

<210> SEQ ID NO 1
<211> LENGTH: 14
<212> TYPE: DNA
<213> ORGANISM: Artificial sequence
<220> FEATURE:
<223> OTHER INFORMATION: Synthetic probe
<220> FEATURE:
<221> NAME/KEY: misc_feature
<222> LOCATION: (9)..(10)
<223> OTHER INFORMATION: exonuclease-resistant modification

<400> SEQUENCE: 1 ttttttttt ttgc                                              14

<210> SEQ ID NO 2
<211> LENGTH: 24
<212> TYPE: DNA
<213> ORGANISM: Artificial sequence
```

```
<220> FEATURE:
<223> OTHER INFORMATION: Synthetic primer

<400> SEQUENCE: 2
cctccctcca ggaagcctac gtga                                              24

<210> SEQ ID NO 3
<211> LENGTH: 22
<212> TYPE: DNA
<213> ORGANISM: Artificial sequence
<220> FEATURE:
<223> OTHER INFORMATION: Synthetic primer
<220> FEATURE:
<221> NAME/KEY: modified_base
<222> LOCATION: (21)..(21)
<223> OTHER INFORMATION: t-butyl benzyl-dC

<400> SEQUENCE: 3
cagtcgaagg gcatgagctg ca                                                22

<210> SEQ ID NO 4
<211> LENGTH: 29
<212> TYPE: DNA
<213> ORGANISM: Artificial sequence
<220> FEATURE:
<223> OTHER INFORMATION: Synthetic probe
<220> FEATURE:
<221> NAME/KEY: misc_feature
<222> LOCATION: (6)..(7)
<223> OTHER INFORMATION: 1,3-propanediol

<400> SEQUENCE: 4 ccccccctg cacggtggag gtgaggcag                                          29

<210> SEQ ID NO 5
<211> LENGTH: 11
<212> TYPE: DNA
<213> ORGANISM: Artificial sequence
<220> FEATURE:
<223> OTHER INFORMATION: Synthetic probe fragment
<220> FEATURE:
<221> NAME/KEY: misc_feature
<222> LOCATION: (9)..(10)
<223> OTHER INFORMATION: exonuclease-resistant modification

<400> SEQUENCE: 5
tttttttttt t                                                            11

<210> SEQ ID NO 6
<211> LENGTH: 10
<212> TYPE: DNA
<213> ORGANISM: Artificial sequence
<220> FEATURE:
<223> OTHER INFORMATION: Synthetic probe fragment
<220> FEATURE:
<221> NAME/KEY: misc_feature
<222> LOCATION: (9)..(10)
<223> OTHER INFORMATION: exo-nuclease resistant modification

<400> SEQUENCE: 6
tttttttttt                                                              10
```

NUCLEIC ACID TARGET IDENTIFICATION BY STRUCTURE BASED PROBE CLEAVAGE

CROSS REFERENCE TO RELATED INVENTION

This application claims the benefit of priority of U.S. Provisional Patent Application Ser. No. 61/799,127, filed Mar. 15, 2013, which is incorporated herein by reference in its entirety.

REFERENCE TO SEQUENCE LISTING

This application contains a Sequence Listing submitted as an electronic text file named "31525_US1_new.txt", having a size in bytes of 2 kb, and created on Jun. 17, 2016. The information contained in this electronic file is hereby incorporated by reference in its entirety pursuant to 37 CFR §1.52(e)(5).

FIELD OF THE INVENTION

The present invention relates to the field of nucleic acid detection. In particular, the present invention provides for a method to perform high throughput multiplex detection of target nucleic acids.

BACKGROUND OF THE INVENTION

Many methods for detection of target nucleic acids are known. Currently available homogeneous assays for nucleic acid detection include the TaqMan®, Amplifluor®, dye-binding, allele-selective kinetic PCR and Scorpion® primer assays. These assay procedures are not readily multiplexed due to the requirement for a different dye for each target nucleic acid to be detected, and thus are limited in their potential for improvement. To overcome such limitations, several recent studies have disclosed the use of oligonucleotide probes containing a cleavable "tag" portion which can be readily separated and detected (e.g. see Chenna et al, U.S. Patent Application Publication No. 2005/0053939; Van Den Boom, U.S. Pat. No. 8,133,701). However the results from these studies show that problems remain in being able to accurately correlate the detection tags with the target nucleic acid and the need still exists for an accurate method to perform high throughput multiplex detection of target nucleic acids.

SUMMARY OF THE INVENTION

The present invention provides for a novel method for nucleic acid sequence detection. In this method, a unique, identifying cleavage fragment from an oligonucleotide probe, bound to a target nucleic acid within the amplification region is produced during PCR by the 5'-nuclease activity of the DNA polymerase. This is achieved by having a non-complementary "flap" region attached to the 5'-end of the probe. The identity of the target nucleic acid can be determined by identifying the unique cleavage fragment. For example, this can be easily accomplished by mass spectroscopy. Due to the extremely large number of possible cleavage fragments with unique and readily resolvable masses, rapid high throughput multiplex detection of nucleic acid targets is thereby made possible.

Therefore in one aspect, the invention provides for a method of detecting the presence or absence of a target nucleic acid sequence in a sample, comprising the steps of:

(a) preparing a reaction mixture by contacting a sample comprising a target nucleic acid with (i) a pair of oligonucleotide primers, wherein a first oligonucleotide primer comprises a sequence complementary to a region in one strand of the target nucleic acid sequence and primes the synthesis of a first extension product, and wherein a second oligonucleotide primer comprises a sequence complementary to a region in said first extension product and primes the synthesis of a nucleic acid strand complementary to said first extension product, and (ii) an oligonucleotide probe comprising at least two distinct portions, a first portion comprised of standard nucleotides with or without nucleotide analogs that comprises a sequence that is at least partially complementary to a region of the target nucleic acid sequence wherein said first portion anneals within the target nucleic acid sequence bounded by said pair of oligonucleotide primers, and wherein said first portion is blocked at the 3' terminus to prohibit extension by a nucleic acid polymerase and to prevent cleavage by a 3' to 5' exonuclease; and a second portion attached to the 5' end of the first portion comprised of either nucleotides or non-nucleotides or both nucleotides and non-nucleotides, and comprises a sequence that is non-complementary to the target nucleic acid sequence, wherein said second portion also comprises an exonuclease-resistant modification;

(b) amplifying said target nucleic acid sequence with a nucleic acid polymerase having 5' to 3' nuclease activity under conditions that allows annealing of said pair of oligonucleotide primers and said oligonucleotide probe to the target nucleic acid sequence and synthesis of primer extension products from said pair of oligonucleotide primers while the 5' to 3' nuclease activity of said nucleic acid polymerase is able to cleave and release from the annealed oligonucleotide probe, fragments containing the second portion of the oligonucleotide probe with or without additional nucleotides from the first portion of the oligonucleotide probe;

(c) treating said fragments containing the second portion of the oligonucleotide probe with a 3' to 5' exonuclease that cleaves said fragments up to the exonuclease-resistant modification thereby producing a single fragment having a unique mass-distinguishable size; and (d) detecting the presence or absence of the single fragment by mass spectrometry, thereby detecting the presence or absence of the target nucleic acid sequence in the sample. In some embodiments, step (d) is preceded by a step of purifying said reaction mixture for removing contaminants of mass spectrometry.

In another aspect, the invention provides for a method of detecting the presence or absence of a target nucleic acid sequence in a sample, comprising the steps of:

(a) preparing a reaction mixture by contacting a sample comprising a target nucleic acid with (i) a pair of oligonucleotide primers, wherein a first oligonucleotide primer comprises a sequence complementary to a region in one strand of the target nucleic acid sequence and primes the synthesis of a first extension product, and wherein a second oligonucleotide primer comprises a sequence complementary to a region in said first extension product and primes the synthesis of a nucleic acid strand complementary to said first extension product, and (ii) an oligonucleotide probe comprising at least two distinct portions, a first portion comprised of standard nucleotides with or without nucleotide analogs that comprises a sequence that is at least partially complementary to a region of the target nucleic acid sequence wherein said first portion anneals within the target nucleic acid sequence bounded by said pair of oligonucleotide primers, wherein the first portion also comprises a modification at the 5'-end that renders it resistant to cleavage by a single strand-specific 5'-3'-exonuclease, and a second portion attached to the 3' end of the first portion comprised of either nucleotides or non-nucleotides or both nucleotides and non-nucleotides, and comprises a sequence that is non-complementary to the target nucleic acid sequence, wherein said second portion also comprises a modification that renders it resistant to cleavage by the single strand-specific 5'-3' exonuclease;

(b) amplifying said target nucleic acid sequence with a nucleic acid polymerase having 5' to 3' nuclease activity under conditions that allows annealing of said pair of oligonucleotide primers and said oligonucleotide probe to the target nucleic acid sequence and synthesis of primer extension products from said pair of oligonucleotide primers while the 5' to 3' nuclease activity of said nucleic acid polymerase is able to cleave and release from the annealed oligonucleotide probe, fragments containing the second portion of the oligonucleotide probe with or without additional nucleotides from the first portion of the oligonucleotide probe;

(c) treating said fragments containing the second portion of the oligonucleotide probe with the single strand-specific 5'-3' exonuclease that cleaves said fragments up to the exonuclease-resistant modification thereby producing a single fragment having a unique mass-distinguishable size; and (d) detecting the presence or absence of the single fragment by mass spectrometry, thereby detecting the presence or absence of the target nucleic acid sequence in the sample. In some embodiments, step (d) is preceded by a step of purifying said reaction mixture for removing contaminants of mass spectrometry.

In another aspect, the invention provides for a composition comprised of an oligonucleotide probe wherein said oligonucleotide probe comprises at least two distinct portions, wherein a first portion is comprised of standard nucleotides with or without nucleotide analogs that comprises a sequence that is at least partially complementary to a region of a target nucleic acid sequence such that said first portion is capable of binding to said region of the target nucleic acid sequence and wherein said first portion is blocked at the 3' terminus to prohibit extension of the said oligonucleotide probe by a DNA polymerase and to prevent cleavage by a 3' to 5' exonuclease; and a second portion attached to the 5' end of the first portion comprised of either nucleotides or non-nucleotides or both nucleotides and non-nucleotides, and comprises a sequence that is non-complementary to the target nucleic acid sequence, wherein said second portion also comprises an exonuclease-resistant modification.

In another aspect, the invention provides for a composition comprised of an oligonucleotide probe wherein said oligonucleotide probe comprises at least two distinct portions, a first portion comprised of standard nucleotides with or without nucleotide analogs that comprises a sequence that is at least partially complementary to a region of the target nucleic acid sequence wherein said first portion anneals within the target nucleic acid sequence bounded by said pair of oligonucleotide primers, wherein the first portion also comprises a modification at the 5'-end that renders it resistant to cleavage by a single strand specific 5'-3'-exonuclease, and a second portion attached to the 3' end of the first portion comprised of either nucleotides or non-nucleotides or both nucleotides and non-nucleotides, and comprises a sequence that is non-complementary to the target nucleic acid sequence, wherein said second portion also comprises a modification that renders it resistant to cleavage by the single strand-specific 5'-3' exonuclease.

In some embodiments, the exonuclease-resistant modification in the second portion of the oligonucleotide probe comprises a non-cleavable nucleotide analog that is selected from the group consisting of phosphorothioate, 2'-O-methyl-ribonucleotide, propanediol spacer, HEG spacer, inverted nucleotide, or any other modification that renders the oligonucleotide fragment resistant to exonucleolytic cleavage beyond the point of attachment of the modification. In other embodiments, the second portion of the oligonucleotide probe is comprised of non-nucleotides that can be any organic moieties or repeat units (e.g. (CH2-CH2-O)n etc.)

DETAILED DESCRIPTION OF THE INVENTION

Definitions

The term "sample" as used herein includes a specimen or culture (e.g., microbiological cultures) that includes nucleic acids. The term "sample" is also meant to include both biological and environmental samples. A sample may include a specimen of synthetic origin. Biological samples include whole blood, serum, plasma, umbilical cord blood, chorionic villi, amniotic fluid, cerebrospinal fluid, spinal fluid, lavage fluid (e.g., bronchioalveolar, gastric, peritoneal, ductal, ear, arthroscopic), biopsy sample, urine, feces, sputum, saliva, nasal mucous, prostate fluid, semen, lymphatic fluid, bile, tears, sweat, breast milk, breast fluid, embryonic cells and fetal cells. In a preferred embodiment, the biological sample is blood, and more preferably plasma. As used herein, the term "blood" encompasses whole blood or any fractions of blood, such as serum and plasma as conventionally defined. Blood plasma refers to the fraction of whole blood resulting from centrifugation of blood treated with anticoagulants. Blood serum refers to the watery portion of fluid remaining after a blood sample has coagulated. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

The terms "target" or "target nucleic acid" as used herein are intended to mean any molecule whose presence is to be detected or measured or whose function, interactions or properties are to be studied. Therefore, a target includes essentially any molecule for which a detectable probe (e.g., oligonucleotide probe) or assay exists, or can be produced by one skilled in the art. For example, a target may be a biomolecule, such as a nucleic acid molecule, a polypeptide, a lipid, or a carbohydrate, that is capable of binding with or otherwise coming in contact with a detectable probe (e.g., an antibody), wherein the detectable probe also comprises nucleic acids capable of being detected by methods of the invention. As used herein, "detectable probe" refers to any molecule or agent capable of hybridizing or annealing to a target biomolecule of interest and allows for the specific detection of the target biomolecule as described herein. In one aspect of the invention, the target is a nucleic acid, and the detectable probe is an oligonucleotide. The terms "nucleic acid" and "nucleic acid molecule" may be used interchangeably throughout the disclosure. The terms refer to oligonucleotides, oligos, polynucleotides, deoxyribonucleotide (DNA), genomic DNA, mitochondrial DNA (mtDNA), complementary DNA (cDNA), bacterial DNA, viral DNA, viral RNA, RNA, message RNA (mRNA), transfer RNA (tRNA), ribosomal RNA (rRNA), siRNA, catalytic RNA, clones, plasmids, M13, P1, cosmid, bacteria artificial chromosome (BAC), yeast artificial chromosome (YAC), amplified nucleic acid, amplicon, PCR product and other types of amplified nucleic acid, RNA/DNA hybrids and polyamide nucleic acids (PNAs), all of which can be in either single- or double-stranded form, and unless otherwise limited, would encompass known analogs of natural nucleotides that can function in a similar manner as naturally occurring nucleotides and combinations and/or mixtures thereof. Thus, the term "nucleotides" refers to both naturally-occurring and modified/nonnaturally-occurring nucleotides, including nucleoside tri, di, and monophosphates as well as monophosphate monomers present within polynucleic acid or oligonucleotide. A nucleotide may also be a ribo; 2'-deoxy; 2',3'-deoxy as well as a vast array of other nucleotide mimics that are well-known in the art. Mimics include chain-terminating nucleotides, such as 3'-O-methyl, halogenated base or sugar substitutions; alternative sugar structures including nonsugar, alkyl ring structures; alternative bases including inosine; deaza-modified; chi, and psi, linker-modified; mass label-modified; phosphodiester modifications or replacements including phosphorothioate, methylphosphonate, boranophosphate, amide, ester, ether; and a basic or complete internucleotide replacements, including cleavage linkages such a photocleavable nitrophenyl moieties.

The presence or absence of a target can be measured quantitatively or qualitatively. Targets can come in a variety of different forms including, for example, simple or complex mixtures, or in substantially purified forms. For example, a target can be part of a sample that contains other components or can be the sole or major component of the sample. Therefore, a target can be a component of a whole cell or tissue, a cell or tissue extract, a fractionated lysate thereof or a substantially purified molecule. Also a target can have either a known or unknown sequence or structure.

The term "amplification reaction" refers to any in vitro means for multiplying the copies of a target sequence of nucleic acid.

"Amplifying" refers to a step of submitting a solution to conditions sufficient to allow for amplification. Components of an amplification reaction may include, but are not limited to, e.g., primers, a polynucleotide template, polymerase, nucleotides, dNTPs and the like. The term "amplifying" typically refers to an "exponential" increase in target nucleic acid. However, "amplifying" as used herein can also refer to linear increases in the numbers of a select target sequence of nucleic acid, but is different than a one-time, single primer extension step.

"Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990.

"Oligonucleotide" as used herein refers to linear oligomers of natural or modified nucleosidic monomers linked by phosphodiester bonds or analogs thereof. Oligonucleotides include deoxyribonucleosides, ribonucleosides, anomeric forms thereof, peptide nucleic acids (PNAs), and the like, capable of specifically binding to a target nucleic acid. Usually monomers are linked by phosphodiester bonds or analogs thereof to form oligonucleotides ranging in size from a few monomeric units, e.g., 3-4, to several tens of monomeric units, e.g., 40-60. Whenever an oligonucleotide is represented by a sequence of letters, such as "ATGCCTG," it will be understood that the nucleotides are in 5'-3' order from left to right and that "A" denotes deoxyadenosine, "C" denotes deoxycytidine, "G" denotes deoxyguanosine, "T" denotes deoxythymidine, and "U" denotes the ribonucleoside, uridine, unless otherwise noted. Usually oligonucleotides comprise the four natural deoxynucleotides; however, they may also comprise ribonucleosides or non-natural nucleotide analogs. Where an enzyme has specific oligonucleotide or polynucleotide substrate requirements for activity, e.g., single stranded DNA, RNA/DNA duplex, or the like, then selection of appropriate composition for the oligonucleotide or polynucleotide substrates is well within the knowledge of one of ordinary skill.

As used herein "oligonucleotide primer", or simply "primer", refers to a polynucleotide sequence that hybridizes to a sequence on a target nucleic acid template and facilitates the detection of an oligonucleotide probe. In amplification embodiments of the invention, an oligonucleotide primer serves as a point of initiation of nucleic acid synthesis. In non-amplification embodiments, an oligonucleotide primer may be used to create a structure that is capable of being cleaved by a cleavage agent. Primers can be of a variety of lengths and are often less than 50 nucleotides in length, for example 12-25 nucleotides, in length. The length and sequences of primers for use in PCR can be designed based on principles known to those of skill in the art.

The term "oligonucleotide probe" as used herein refers to a polynucleotide sequence capable of hybridizing or annealing to a target nucleic acid of interest and allows for the specific detection of the target nucleic acid.

A "mismatched nucleotide" or a "mismatch" refers to a nucleotide that is not complementary to the target sequence at that position or positions. An oligonucleotide probe may have at least one mismatch, but can also have 2, 3, 4, 5, 6 or 7 or more mismatched nucleotides.

The term "polymorphism" as used herein refers to an allelic variant. Polymorphisms can include single nucleotide polymorphisms (SNP's) as well as simple sequence length polymorphisms. A polymorphism can be due to one or more nucleotide substitutions at one allele in comparison to another allele or can be due to an insertion or deletion, duplication, inversion and other alterations known to the art.

The term "mass-distinguishable size" as used herein may be used interchangeably with "cleavage product size", "degradation product size" or "probe fragment size" and refers to the size of one or more degradation products resulting from the cleavage and release of the oligonucleotide probe as described by the methods herein. Fragments having mass-distinguishable sizes (MDF) may include, but are not limited to, oligonucleotide probe fragments, nucleotide oligonucleotide probe fragments, non-nucleotide oligonucleotide probe fragments, oligonucleotide probe fragments containing modification tags to facilitate separation (e.g. hydrophobic and affinity moieties). Producing a fragment with a unique mass-distinguishable size results in significantly improved sensitivity and allows for an enhanced ability to perform multiplex reaction.

The term "modification" as used herein refers to alterations of the oligonucleotide probe at the molecular level (e.g., base moiety, sugar moiety or phosphate backbone). Nucleoside modifications include, but are not limited to, the introduction of cleavage blockers or cleavage inducers, the introduction of minor groove binders, isotopic enrichment, isotopic depletion, the introduction of deuterium, and halogen modifications. Nucleoside modifications may also include moieties that increase the stringency of hybridization or increase the melting temperature of the oligonucleotide probe. For example, a nucleotide molecule may be modified with an extra bridge connecting the 2' and 4' carbons resulting in locked nucleic acid (LNA) nucleotide that is resistant to cleavage by a nuclease.

The term "specific" or "specificity" in reference to the binding of one molecule to another molecule, such as a probe for a target polynucleotide, refers to the recognition, contact, and formation of a stable complex between the two molecules, together with substantially less recognition, contact, or complex formation of that molecule with other molecules. As used herein, the term "anneal" refers to the formation of a stable complex between two molecules.

A probe is "capable of annealing" to a nucleic acid sequence if at least one region of the probe shares substantial sequence identity with at least one region of the complement of the nucleic acid sequence. "Substantial sequence identity" is a sequence identity of at least about 80%, preferably at least about 85%, more preferably at least about 90%, 95% or 99%, and most preferably 100%. For the purpose of determining sequence identity of a DNA sequence and a RNA sequence, U and T often are considered the same nucleotide. For example, a probe comprising the sequence ATCAGC is capable of hybridizing to a target RNA sequence comprising the sequence GCUGAU.

The term "cleavage agent" as used herein refers to any means that is capable of cleaving an oligonucleotide probe to yield fragments of mass-distinguishable sizes, including but not limited to enzymes. For methods wherein amplification does not occur, the cleavage agent may serve solely to cleave, degrade or otherwise release the second portion of the oligonucleotide probe or fragments thereof. The cleavage agent may be an enzyme. The cleavage agent may be natural, synthetic, unmodified or modified.

For methods wherein amplification occurs, the cleavage agent is preferably an enzyme that possess synthetic (or polymerization) activity and nuclease activity. Such an enzyme is often a nucleic acid amplification enzyme. An example of a nucleic acid amplification enzyme is a nucleic acid polymerase enzyme such as Thermus aquaticus (Taq) DNA polymerase (TaqMAN®) or E. coli DNA polymerase I. The enzyme may be naturally occurring, unmodified or modified.

The term "cleaves said fragments up to the exonuclease-resistant modification" means a cleavage activity that would cleave the fragments until reaching the exonuclease-resistant modification itself or at a defined nucleotide located proximal to the exonuclease-resistant modification. For a 3' to 5' exonuclease activity, the defined nucleotide proximal to the modification could be located at the first position immediately 3' from the modification. Alternatively, the defined nucleotide could be located two or three or even more positions 3' from the modification, so long as cleavage by the 3' to 5' exonuclease consistently terminates at the position of the defined nucleotide.

The term "propanediol" or "propanediol spacer" refers to 1,3-Propanediol and is synonymous with Propane-1,3-diol, 1,3-Dihydroxypropane, and Trimethylene glycol. The term "HEG" or "HEG spacer" refers to hexaethylene glycol, which is synonymous with 3,6,9,12,15-Pentaoxaheptadecane-1,17-diol. The term inverted nucleotide refers to a nucleotide in which the sugar moiety is linked to the sugar moiety of an adjacent nucleotide via a 3' to 3' phosphodiester linkage.

The term "contaminants of mass spectrometry" refers to any substance capable of interfering with the detection of a fragment with a mass-distinguishable size (MDF) by a mass spectrometer. Examples of some contaminants of mass spectrometry are disclosed in Keller et al., *Analytica Chimica Acta* (2008) 627:71-81.

A "nucleic acid polymerase" refers to an enzyme that catalyzes the incorporation of nucleotides into a nucleic acid. Exemplary nucleic acid polymerases include DNA polymerases, RNA polymerases, terminal transferases, reverse transcriptases, telomerases and the like.

A "thermostable DNA polymerase" refers to a DNA polymerase that is stable (i.e., resists breakdown or denaturation) and retains sufficient catalytic activity when subjected to elevated temperatures for selected periods of time. For example, a thermostable DNA polymerase retains sufficient activity to effect subsequent primer extension reactions, when subjected to elevated temperatures for the time necessary to denature double-stranded nucleic acids. Heating conditions necessary for nucleic acid denaturation are well known in the art and are exemplified in U.S. Pat. Nos. 4,683,202 and 4,683,195. As used herein, a thermostable polymerase is typically suitable for use in a temperature cycling reaction such as the polymerase chain reaction ("PCR"). The examples of thermostable nucleic acid polymerases include *Thermus aquaticus* Taq DNA polymerase, *Thermus* sp. Z05 polymerase, *Thermus flavus* polymerase, *Thermotoga maritima* polymerases, such as TMA-25 and TMA-30 polymerases, Tth DNA polymerase, and the like.

A "modified" polymerase refers to a polymerase in which at least one monomer differs from the reference sequence, such as a native or wild-type form of the polymerase or another modified form of the polymerase. Exemplary modifications include monomer insertions, deletions, and substitutions. Modified polymerases also include chimeric polymerases that have identifiable component sequences (e.g., structural or functional domains, etc.) derived from two or more parents. Also included within the definition of modified polymerases are those comprising chemical modifications of the reference sequence. The examples of modified polymerases include G46E E678G CS5 DNA polymerase, G46E L329A E678G CS5 DNA polymerase, G46E L329A D640G S671F CS5 DNA polymerase, G46E L329A D640G S671F E678G CS5 DNA polymerase, a G46E E678G CS6 DNA polymerase, Z05 DNA polymerase, ΔZ05 polymerase, ΔZ05-Gold polymerase, ΔZ05R polymerase, E615G Taq DNA polymerase, E678G TMA-25 polymerase, E678G TMA-30 polymerase, and the like.

The term "5' to 3' nuclease activity" or "5'-3' nuclease activity" refers to an activity of a nucleic acid polymerase, typically associated with the nucleic acid strand synthesis, whereby nucleotides are removed from the 5' end of nucleic acid strand, e.g., *E. coli* DNA polymerase I has this activity, whereas the Klenow fragment does not. Some enzymes that have 5' to 3' nuclease activity are 5' to 3' exonucleases. The term "single strand-specific 5'-3' exonuclease" refers to exonucleases acting from the 5' end with a preference for single stranded nucleic acids over double stranded nucleic acids. Examples of such single strand-specific 5'-3' exonucleases include: Exonuclease from *B. subtilis*, Phosphodiesterase from spleen, Exonuclease II from yeast, Exonuclease V from yeast, and Exonuclease from *Neurospora crassa*.

The term "3' to 5' exonuclease" or "3' to 5' exonuclease activity" refers to an enzyme or an activity of an enzyme, whereby nucleotides are removed from the 3' end of the nucleic acid strand. Examples of 3' to 5' exonucleases include: Exonuclease I from *E. coli*, Exonuclease IV from *E. coli*, Exonuclease V from *E. coli*, T4 Exonuclease IV from Phage T4, T4 DNA Polymerase from Phage T4, Exonuclease I from Yeast, Exonuclease III from Yeast, DNA Polymerase I from *E. coli*, Klenow fragment, DNA polymerase α from *Drosophila*, DNA polymerase γ from *Drosophila*, and Snake venom phosphodiesterase.

Various aspects of the present invention are based on a special property of nucleic acid polymerases. Nucleic acid polymerases can possess several activities, among them, a 5' to 3' nuclease activity whereby the nucleic acid polymerase can cleave mononucleotides or small oligonucleotides from an oligonucleotide annealed to its larger, complementary polynucleotide. In order for cleavage to occur efficiently, an upstream oligonucleotide must also be annealed to the same larger polynucleotide.

The detection of a target nucleic acid utilizing the 5' to 3' nuclease activity can be performed by a "TaqMan®" or "5'-nuclease assay", as described in U.S. Pat. Nos. 5,210,015; 5,487,972; and 5,804,375; and Holland et al., 1988, Proc. Natl. Acad. Sci. USA 88:7276-7280, all incorporated by reference herein. In the TaqMan® assay, labeled detection probes that hybridize within the amplified region are present during the amplification reaction. The probes are modified so as to prevent the probes from acting as primers for DNA synthesis. The amplification is performed using a DNA polymerase having 5' to 3' nuclease activity on double stranded nucleic acids. During each synthesis step of the amplification, any probe which hybridizes to the target nucleic acid downstream from the primer being extended is degraded by the 5' to 3' nuclease activity of the DNA polymerase. Thus, the synthesis of a new target strand also results in the degradation of a probe, and the accumulation of degradation product provides a measure of the synthesis of target sequences.

Any method suitable for detecting degradation product can be used in a 5' nuclease assay. Often, the detection probe is labeled with two fluorescent dyes, one of which is capable of quenching the fluorescence of the other dye. The dyes are attached to the probe, typically with the reporter or detector dye attached to the 5' terminus and the quenching dye attached to an internal site, such that quenching occurs when the probe is in an unhybridized state and such that cleavage of the probe by the 5' to 3' nuclease activity of the DNA polymerase occurs in between the two dyes. Amplification results in cleavage of the probe between the dyes with a concomitant elimination of quenching and an increase in the fluorescence observable from the initially quenched dye. The accumulation of degradation product is monitored by measuring the increase in reaction fluorescence. U.S. Pat. Nos. 5,491,063 and 5,571,673, both incorporated by reference herein, describe alternative methods for detecting the degradation of probe which occurs concomitant with amplification.

A 5' nuclease assay for the detection of a target nucleic acid can employ any polymerase that has a 5' to 3' nuclease activity. Thus, in some embodiments, the polymerases with 5'-nuclease activity are thermostable and thermoactive nucleic acid polymerases. Such thermostable polymerases include, but are not limited to, native and recombinant forms of polymerases from a variety of species of the eubacterial genera *Thermus, Thermatoga,* and *Thermosipho*, as well as chimeric forms thereof example, *Thermus* species polymerases that can be used in the methods of the invention include *Thermus aquaticus* (Taq) DNA polymerase, *Thermus thermophilus* (Tth) DNA polymerase, *Thermus* species Z05 (Z05) DNA polymerase, *Thermus* species sps17 (sps17), and *Thermus* species Z05 (e.g., described in U.S. Pat. Nos. 5,405,774; 5,352,600; 5,079,352; 4,889,818; 5,466,591; 5,618,711; 5,674,738, and 5,795,762. *Thermatoga* polymerases that can be used in the methods of the invention include, for example, *Thermatoga maritima* DNA polymerase and *Thermatoga neapolitana* DNA polymerase, while an example of a *Thermosipho* polymerase that can be used is *Thermosipho africanus* DNA polymerase. The sequences of *Thermatoga maritima* and *Thermosipho africanus* DNA polymerases are published in International Patent Application No. PCT/US91/07035 with Publication No. WO 92/06200. The sequence of *Thermatoga neapolitana* may be found in International Patent Publication No. WO 97/09451.

In the 5' nuclease assay, the amplification detection is typically concurrent with amplification (i.e., "real-time"). In some embodiments the amplification detection is quantitative, and the amplification detection is real-time. In some embodiments, the amplification detection is qualitative (e.g., end-point detection of the presence or absence of a target nucleic acid). In some embodiments, the amplification detection is subsequent to amplification. In some embodiments, the amplification detection is qualitative, and the amplification detection is subsequent to amplification.

In the present invention, detection of the degradation products from the oligonucleotide probe does not involve the use of fluorescent reporter dyes and quenching dyes but instead involves the synthesis of the probe to have two distinct portions. The first portion is a complementary portion that is at least partially complementary to a target nucleic acid and is composed of standard nucleotides or nucleotide analogs, such that this portion is capable of binding to the target nucleic acid to be detected. Furthermore, the 3' terminus of this first portion of the probe is modified or blocked such that it cannot be extended by the DNA polymerase and cannot be cleaved by a 3' to 5' exonuclease. The second portion is a non-complementary portion that is attached to the 5' end of the first portion and forms a "5' flap" region that is not capable of binding to the target nucleic acid (see FIG. 1). This 5' flap portion can be comprised of nucleotides or non-nucleotides or both nucleotides and non-nucleotides. Non-nucleotides that can be present in the 5' flap second portion of the oligonucleotide probe can be any organic moieties, or repeat units (e.g. (CH2-CH2-O)n, etc.) The second portion also contains a modification that makes it resistant to the activity of a 3' to 5' exonuclease (shown as "X" in FIG. 1). This modification can be a nucleotide analog which is non-cleavable by a 3' to 5' exonuclease and examples of such a nucleotide analog include phosphorothioate, 2'-O-methyl-ribonucleotide, propanediol spacer, HEG spacer, inverted nucleotide, or any other modification that renders the oligonucleotide fragment resistant to exonucleolytic cleavage beyond the point of attachment of the modification.

The present invention provides for oligonucleotide primers and probes. It is not intended that the methods used to produce these probes and primers be in any way limited. One of skill in the art is well familiar with the wide variety of chemical synthesis strategies and reagents for producing probes and primers. It is also not intended that the oligonucleotide probes of the invention be limited to limited to naturally occurring nucleotide structures or naturally occurring bases (e.g., adenine, guanine, thymine, cytosine, and uracil). In addition to the naturally occurring heterocyclic bases that are typically found in nucleic acids, non-natural nucleic acid analogs also find use with the invention.

Non-natural analogs include those having non-naturally occurring heterocyclic or other modified bases. In particular, many non-naturally occurring bases are described further in, e.g., Seela et al. (1991) Helv. Chim. Acta 74:1790, Grein et al. (1994) Bioorg. Med. Chem. Lett. 4:971-976, and Seela et al. (1999) Helv. Chim. Acta 82:1640. To further illustrate, certain bases used in nucleotides that act as melting temperature (Tm) modifiers are optionally included. For example, some of these include 7-deazapurines (e.g., 7-deazaguanine, 7-deazaadenine, etc.), pyrazolo[3,4-d]pyrimidines, propynyl-dN (e.g., propynyl-dU, propynyl-dC, etc.), and the like. See, e.g., U.S. Pat. No. 5,990,303, entitled "SYNTHESIS OF 7-DEAZA-2'-DEOXYGUANOSINE NUCLEOTIDES," which issued Nov. 23, 1999 to Seela. Other representative heterocyclic bases include, e.g., hypoxanthine, inosine, xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytosine; 5-fluorocytosine; 5-chlorocytosine; 5-iodocytosine; 5-bromocytosine; 5-methylcytosine; 5-propynylcytosine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil, 4-acetylcytosine, 5-(carboxyhydroxymethyl)uracil, 5 carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 7-deazaadenine, 2-methyladenine, 2-methylguanine, 3-methylcytosine, 5-methylcytosine, N6-methyladenine, 7-methylguanine, 7-deazaguanine, 5-methylaminomethyluracil, 5-methoxyaminomethyl-2-thiouracil, beta-D mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2 thiocytosine, 5-methyl-2-thiouracil, 2-thiouracil, 4-thiouracil, 5-methyluracil, uracil-5-oxyacetic acidmethylester, 3-(3-amino-3-N-2-carboxypropyl) uracil, (acp3)w, 2,6-diaminopurine, and 5-propynyl pyrimidine, and the like. To further illustrate, other examples of modified oligonucleotides include those having one or more locked nucleid acid (LNA™) monomers (oligonucleotides comprising LNA™ monomers available from, e.g., Link Technologies, Ltd., Lanarkshire, Scotland; under license from Exiqon A/S, Vedbaek, Denmark). Nucleotide analogs such as these are also described in, e.g., U.S. Pat. No. 6,639,059, entitled "SYNTHESIS OF [2.2.1]BICYCLO NUCLEOSIDES," issued Oct. 28, 2003 to Kochkine et al., U.S. Pat. No. 6,303,315, entitled "ONE STEP SAMPLE PREPARATION AND DETECTION OF NUCLEIC ACIDS IN COMPLEX BIOLOGICAL SAMPLES," issued Oct. 16, 2001 to Skouv, and U.S. Pat. Application Pub. No. 2003/0092905, entitled "SYNTHESIS OF [2.2.1]BICYCLO NUCLEOSIDES," by Kochkine et al. that published May 15, 2003, which are each incorporated by reference.

Oligonucleotide probes and primers can be prepared using any technique known in the art. In certain embodiments, for example, the oligonucleotide probes and primers are synthesized chemically using any nucleic acid synthesis method, including, e.g., according to the solid phase phosphoramidite method described by Beaucage and Caruthers (1981) Tetrahedron Letts. 22(20):1859 1862, which is incorporated by reference. To further illustrate, oligonucleotides can also be synthesized using a triester method (see, e.g., Capaldi et al. (2000) "Highly efficient solid phase synthesis of oligonucleotide analogs containing phosphorodithioate linkages" Nucleic Acids Res. 28(9):e40 and Eldrup et al. (1994) "Preparation of oligodeoxyribonucleoside phosphorodithioates by a triester method" Nucleic Acids Res. 22(10):1797-1804, which are both incorporated by reference). Other synthesis techniques known in the art can also be utilized, including, e.g., using an automated synthesizer, as described in Needham VanDevanter et al. (1984) Nucleic Acids Res. 12:6159 6168, which is incorporated by reference. A wide variety of equipment is commercially available for automated oligonucleotide synthesis. Multi-nucleotide synthesis approaches (e.g., tri-nucleotide synthesis, etc.) are also optionally utilized. Moreover, the primer nucleic acids optionally include various modifications. In certain embodiments, for example, primers include restriction site linkers, e.g., to facilitate subsequent amplicon cloning or the like. To further illustrate, primers are also optionally modified to improve the specificity of amplification reactions as described in, e.g., U.S. Pat. No. 6,001,611, entitled "MODIFIED NUCLEIC ACID AMPLIFICATION PRIMERS," issued Dec. 14, 1999 to Will, which is incorporated by reference. Primers and probes can also be synthesized with various other modifications as described herein or as otherwise known in the art.

Probes utilized in the reaction mixtures, methods, and other aspects of the invention may have nucleotide or non-nucleotide tags. Such tags can be attached to oligonucleotides directly or indirectly by a variety of techniques known in the art. To illustrate, depending on the type of tag used, the tag can be attached to a terminal (5' or 3' end of an oligonucleotide primer and/or probe) or a non-terminal nucleotide, and can be attached indirectly through linkers or spacer arms of various sizes and compositions. Using commercially available phosphoramidite reagents, one can produce oligonucleotides containing functional groups (e.g., thiols or primary amines) at either the 5' or 3' terminus via an appropriately protected phosphoramidite, and can attach tags to such oligonucleotides using protocols described in, e.g., Innis et al. (Eds.) PCR Protocols: A Guide to Methods and Applications, Elsevier Science & Technology Books (1990)(Innis), which is incorporated by reference.

Essentially any nucleic acid (standard or non-standard, labeled or non-labeled) can be custom or standard ordered from any of a variety of commercial sources, such as The Midland Certified Reagent Company (Midland, Tex.), Operon Technologies Inc. (Huntsville, Ala.), Proligo LLC (Boulder, Colo.), and many others.

Figure 1:
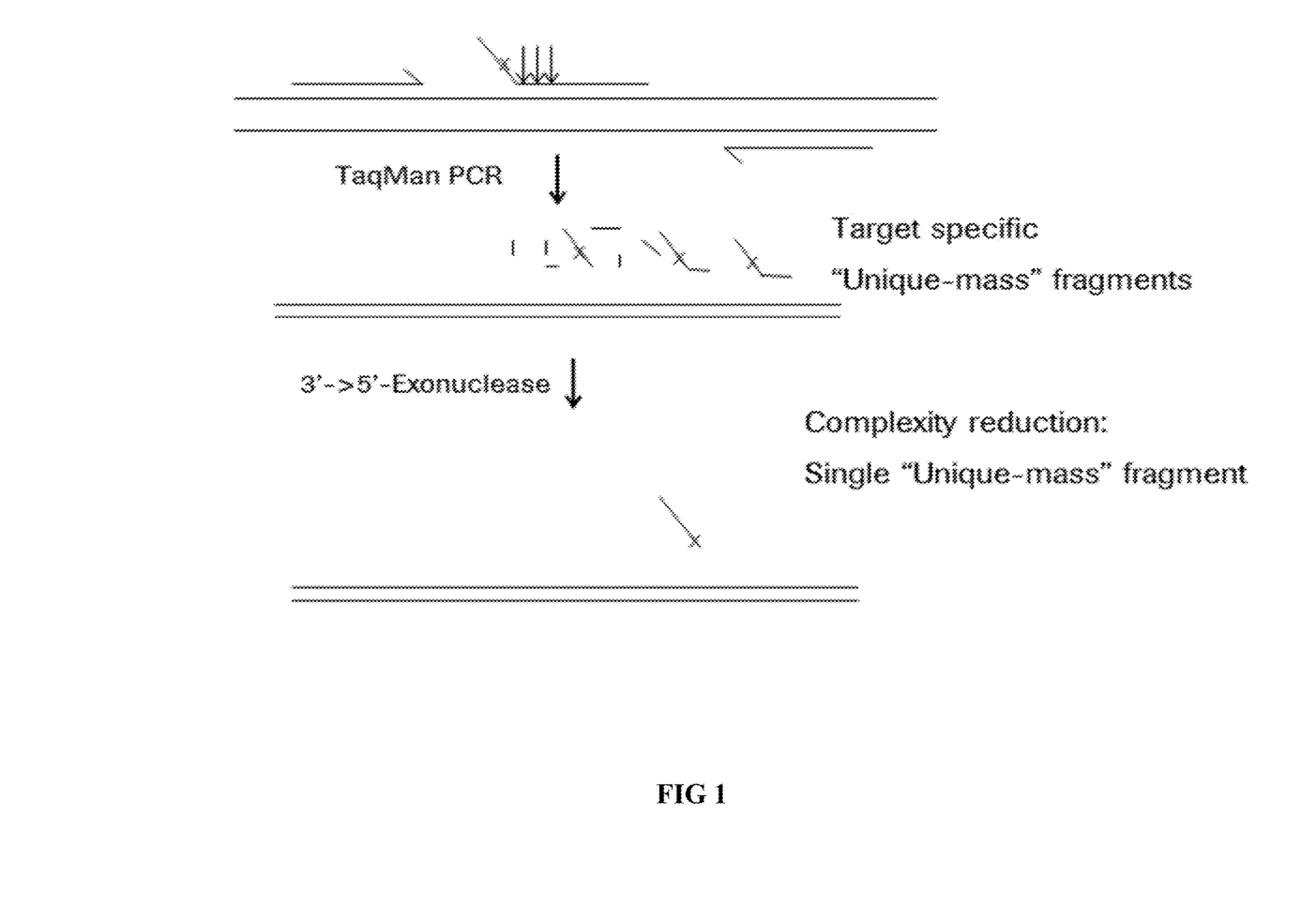
FIG. 1 represents an illustrative description of the methods of the present invention.

Using the oligonucleotide probe of the present invention in a TaqMan PCR assay results in the generation of multiple fragments of the probe due to the multiple cleavage sites in the annealed, first portion of the probe (FIG. 1). Although these fragments would yield a "mass-distinguishable signature" for a given target nucleic acid in subsequent detection by mass spectrometry, the presence of multiple target nucleic acids in a sample (e.g. multiplex assay with more than ten target nucleic acids) would generate a huge number of the "mass-distinguishable signature" fragments such that fragments with very similar masses originating from different target nucleic acids would appear. Thus accurate identification of the presence or absence of a particular target nucleic acid would be difficult. This problem is solved by providing a treatment step using a 3' to 5' exonuclease which would cleave the fragments until reaching the exonuclease-resistant modification itself or at a defined nucleotide located to the 3' side to the exonuclease-resistant modification on the 5' flap portion and not cleave the fragments any further. As a result, a single "unique-mass" fragment would be generated for each individual target nucleic acid and would be detected by mass spectrometry.

Fragments with mass-distinguishable sizes (MDF) are distinguished by a particular physical attribute or detection feature, including but not limited to length, mass, charge, or charge-to-mass ratio. In a preferred embodiment, the detection feature is mass. In another related embodiment, the MDF may be distinguished by a behavior that is related to a physical attribute, including but not limited to mass, time of flight in MALDI-TOF mass spectrometry. In a related embodiment, MDF's from one or more oligonucleotide probes are released and selectively desorbed from a mass spectral matrix such that the non-selective primers and oligonucleotide probes (i.e., the target nucleic acid is not present) do not desorb. For these embodiments, the MDFs should desorb more efficiently from the mass spectral matrix than oligonucleotide probes or other non-MDF's present in the reaction mixture. Preferred mass spectral matrices include 2,5-dihydroxybenzoic acid, alpha-cyano-4-hydroxycinammic acid, 3-hydroxypicolinic acid (3-HPA), diammoniumcitrate (DAC) and combinations thereof. In another embodiment, the mass spectral matrices may be designed for the analysis of proteins. Exemplary matrices for protein analysis include, but are not limited to, DHB and CHCA.

The method can further include an additional step of separating one or more oligonucleotide probe fragments (i.e., MDFs) from un-cleaved or partially-cleaved oligonucleotide probes. Separation can be accomplished using capture ligands, such as biotin or other affinity ligands, and capture agents, such as avidin, streptavidin, an antibody, a receptor, a capture probe that is complementary to the MDF, or a functional fragment thereof, having specific binding activity to the capture ligand. A MDF can contain a capture ligand having specific binding activity for a capture agent. A capture ligand and capture agent can also be used to add mass to the remaining part of the MDF such that it can be excluded from the mass range of the MDF detected in a mass spectrometer. In one embodiment, the capture probe may have a universal primer for universal amplification of cleavage product.

A separation step can also be used to remove salts, enzymes, or other buffer components from the MDFs. Several methods well known in the art, such as chromatography, gel electrophoresis, or precipitation, can be used to clean up the sample. For example, size exclusion chromatography or affinity chromatography can be used to remove salt from a sample. The choice of separation method can depend on the amount of a sample. For example, when small amounts of sample are available or a miniaturized apparatus is used, a micro-affinity chromatography separation step can be used. In addition, whether a separation step is desired, and the choice of separation method, can depend on the detection method used. For example, the efficiency of matrix-assisted laser desorption/ionization and electrospray ionization can be improved by removing salts from a sample. For example, salts can absorb energy from the laser in matrix-assisted laser desorption/ionization and result in lower ionization efficiency.

Mass spectrometry is the preferred method to detect fragments with mass-distinguishable sizes (MDFs) of the invention and thus identify and/or quantitate target nucleic acids. MDFs can be ionized in a mass spectrometer and the ions separated in space or time based on their mass-to-charge ratio. The mass spectrometer then calculates a mass associated with each ion. Therefore, when referring to mass spectrometry, the term mass can be used for simplicity to describe a mass-to-charge ratio.

Mass spectrometry is a sensitive and accurate technique for separating and identifying molecules. Generally, mass spectrometers have two main components, an ion source for the production of ions and a mass-selective analyzer for measuring the mass-to-charge ratio of ions, which is and converted into a measurement of mass for these ions. Several ionization methods are known in the art and described herein. A MDF can be charged prior to, during or after cleavage from the oligonucleotide probe. Consequently, a MDF that will be measured by mass spectrometry does not always require a charge since a charge can be acquired through the mass spectrometry procedure. In mass spectrometry analysis, optional components of a MDF such as charge and detection moieties can be used to contribute mass to the MDF.

Different mass spectrometry methods, for example, quadrupole mass spectrometry, ion trap mass spectrometry, time-of-flight mass spectrometry, gas chromatography mass spectrometry and tandem mass spectrometry, as described herein, can utilize various combinations of ion sources and mass analyzers which allows for flexibility in designing customized detection protocols. In addition, mass spectrometers can be programmed to transmit all ions from the ion source into the mass spectrometer either sequentially or at the same time. Furthermore, a mass spectrometer can be programmed to select ions of a particular mass for transmission into the mass spectrometer while blocking other ions.

The ability to precisely control the movement of ions in a mass spectrometer allows for greater options in detection protocols which can be advantageous when a large number of mMDFs, for example, from a multiplex experiment, are being analyzed. For example, in a multiplex experiment with a large number of MDFs it can be advantageous to select individual reporters from a group of similar reporters and then analyze that reporter separately. Another advantage based on controlling the mass range detected by the mass spectrometer includes the ability to exclude un-cleaved or partially-cleaved tagged probes from being analyzed which reduces background noise from the assay.

Mass spectrometers can resolve ions with small mass differences and measure the mass of ions with a high degree of accuracy. Therefore, MDFs of similar masses can be used together in the same experiment since the mass spectrometer can differentiate the mass of even closely related tags. The high degree of resolution and mass accuracy achieved using mass spectrometry methods allows the use of large sets of tagged probes because the resulting reporter tags can be distinguished from each other. The ability to use large sets of tagged probes is an advantage when designing multiplex experiments.

Another advantage of using mass spectrometry for detecting the mass of a MDF is based on the high sensitivity of this type of mass analysis. Mass spectrometers achieve high sensitivity by utilizing a large portion of the ions that are formed by the ion source and efficiently transmitting these ions through the mass analyzer to the detector. Because of this high level of sensitivity, even limited amounts of sample can be measured using mass spectrometry. This can be an advantage in a multiplex experiment where the amount of each MDF species may be small.

Mass spectrometry methods are well known in the art (see Burlingame et al. Anal. Chem. 70:647R-716R (1998); Kinter and Sherman, Protein Sequencing and Identification Using Tandem Mass Spectrometry Wiley-Interscience, New York (2000)). The basic processes associated with a mass spectrometry method are the generation of gas-phase ions derived from the sample, and the measurement of their mass.

The movement of gas-phase ions can be precisely controlled using electromagnetic fields generated in the mass spectrometer. The movement of ions in these electromagnetic fields is proportional to the m/z of the ion and this forms the basis of measuring the m/z and therefore the mass of a sample. The movement of ions in these electromagnetic fields allows the ions to be contained and focused which accounts for the high sensitivity of mass spectrometry. During the course of m/z measurement, ions are transmitted with high efficiency to particle detectors that record the arrival of these ions. The quantity of ions at each m/z is demonstrated by peaks on a graph where the x axis is m/z and the y axis is relative abundance. Different mass spectrometers have different levels of resolution, that is, the ability to resolve peaks between ions closely related in mass. The resolution is defined as R=m/delta m, where m is the ion mass and delta m is the difference in mass between two peaks in a mass spectrum. For example, a mass spectrometer with a resolution of 1000 can resolve an ion with a m/z of 100.0 from an ion with a m/z of 100.1.

Several types of mass spectrometers are available or can be produced with various configurations. In general, a mass spectrometer has the following major components: a sample inlet, an ion source, a mass analyzer, a detector, a vacuum system, and instrument-control system, and a data system. Difference in the sample inlet, ion source, and mass analyzer generally define the type of instrument and its capabilities. For example, an inlet can be a capillary-column liquid chromatography source or can be a direct probe or stage such as used in matrix-assisted laser desorption. Common ion sources are, for example, electrospray, including nanospray and microspray or matrix-assisted laser desorption. Exemplary mass analyzers include a quadrupole mass filter, ion trap mass analyzer and time-of-flight mass analyzer.

The ion formation process is a starting point for mass spectrum analysis. Several ionization methods are available and the choice of ionization method depends on the sample to be analyzed. For example, for the analysis of polypeptides a relatively gentle ionization procedure such as electrospray ionization (ESI) can be desirable. For ESI, a solution containing the sample is passed through a fine needle at high potential which creates a strong electrical field resulting in a fine spray of highly charged droplets that is directed into the mass spectrometer. Other ionization procedures include, for example, fast-atom bombardment (FAB) which uses a high-energy beam of neutral atoms to strike a solid sample causing desorption and ionization. Matrix-assisted laser desorption ionization (MALDI) is a method in which a laser pulse is used to strike a sample that has been crystallized in an UV-absorbing compound matrix. Other ionization procedures known in the art include, for example, plasma and glow discharge, plasma desorption ionization, resonance ionization, and secondary ionization. A MDF can become ionized prior to, during, or after cleavage from the tagged probe.

Electrospray ionization (ESI) has several properties that are useful for the invention described herein. For example, ESI can be used for biological molecules such as polypeptides that are difficult to ionize or vaporize. In addition, the efficiency of ESI can be very high which provides the basis for highly sensitive measurements. Furthermore, ESI produces charged molecules from solution, which is convenient for analyzing MDFs that are in solution. In contrast, ionization procedures such as MALDI require crystallization of the sample prior to ionization.

Since ESI can produce charged molecules directly from solution, it is compatible with samples from liquid chromatography systems. For example, a mass spectrometer can have an inlet for a liquid chromatography system, such as an HPLC, so that fractions flow from the chromatography column into the mass spectrometer. This in-line arrangement of a liquid chromatography system and mass spectrometer is sometimes referred to as LC-MS. A LC-MS system can be used, for example, to separate un-cleaved or partially cleaved MDFs from cleaved MDF's before mass spectrometry analysis. In addition, chromatography can be used to remove salts or other buffer components from the MDF sample before mass spectrometry analysis. For example, desalting of a sample using a reversed-phase HPLC column, in-line or off-line, can be used to increase the efficiency of the ionization process and thus improve sensitivity of detection by mass spectrometry.

A variety of mass analyzers are available that can be paired with different ion sources. Different mass analyzers have different advantages as known to one skilled in the art and as described herein. The mass spectrometer and methods chosen for detection depends on the particular assay, for example, a more sensitive mass analyzer can be used when a small amount of ions are generated for detection. Several types of mass analyzers and mass spectrometry methods are described below.

Ion mobility mass (IM) spectrometry is a gas-phase separation method that adds new dimensions to mass spectrometry (MS). IM separates gas-phase ions based on their collision cross-section and can be coupled with time-of-flight (TOF) mass spectrometry to yield a powerful tool used in the identification and characterization of proteins and peptides. Therefore, IM-MS has particular utility for the present invention when the MDF is a protein or peptide. IM-MS is discussed in more detail by Verbeck et al. in the Journal of Biomolecular Techniques (Vol 13, Issue 2, 56-61).

Quadrupole mass spectrometry utilizes a quadrupole mass filter or analyzer. This type of mass analyzer is composed of four rods arranged as two sets of two electrically connected rods. A combination of rf and dc voltages are applied to each pair of rods which produces fields that cause an oscillating movement of the ions as they move from the beginning of the mass filter to the end. The result of these fields is the production of a high-pass mass filter in one pair of rods and a low-pass filter in the other pair of rods. Overlap between the high-pass and low-pass filter leaves a defined m/z that can pass both filters and traverse the length of the quadrupole. This m/z is selected and remains stable in the quadrupole mass filter while all other m/z have unstable trajectories and do not remain in the mass filter. A mass spectrum results by ramping the applied fields such that an increasing m/z is selected to pass through the mass filter and reach the detector. In addition, quadrupoles can also be set up to contain and transmit ions of all m/z by applying a rf-only field. This allows quadrupoles to function as a lens or focusing system in regions of the mass spectrometer where ion transmission is needed without mass filtering. This will be of use in tandem mass spectrometry as described further below.

A quadrupole mass analyzer, as well as the other mass analyzers described herein, can be programmed to analyze a defined m/z or mass range. This property of mass spectrometers is useful for the invention described herein. Since the mass range of cleaved MDF will be known prior to an assay, a mass spectrometer can be programmed to transmit ions of the projected correct mass range while excluding ions of a higher or lower mass range. The ability to select a mass range can decrease the background noise in the assay and thus increase the signal-to-noise ratio. In addition, a defined mass range can be used to exclude analysis of any un-cleaved oligonucleotide probes, which would be of higher mass than the mass of the MDFs. Therefore, the mass spectrometer can accomplish an inherent separation step as well as detection and identification of the MDFs Ion trap mass spectrometry utilizes an ion trap mass analyzer. In these mass analyzers, fields are applied so that ions of all m/z are initially trapped and oscillate in the mass analyzer. Ions enter the ion trap from the ion source through a focusing device such as an octapole lens system. Ion trapping takes place in the trapping region before excitation and ejection through an electrode to the detector. Mass analysis is accomplished by sequentially applying voltages that increase the amplitude of the oscillations in a way that ejects ions of increasing m/z out of the trap and into the detector. In contrast to quadrupole mass spectrometry, all ions are retained in the fields of the mass analyzer except those with the selected m/z. One advantage to ion traps is that they have very high sensitivity, as long as one is careful to limit the number of ions being tapped at one time. Control of the number of ions can be accomplished by varying the time over which ions are injected into the trap. The mass resolution of ion traps is similar to that of quadrupole mass filters, although ion traps do have low m/z limitations.

Time-of-flight mass spectrometry utilizes a time-of-flight mass analyzer. For this method of m/z analysis, an ion is first given a fixed amount of kinetic energy by acceleration in an electric field (generated by high voltage). Following acceleration, the ion enters a field-free or "drift" region where it travels at a velocity that is inversely proportional to its m/z. Therefore, ions with low m/z travel more rapidly than ions with high m/z. The time required for ions to travel the length of the field-free region is measured and used to calculate the m/z of the ion.

One consideration in this type of mass analysis is that the set of ions being studied be introduced into the analyzer at the same time. For example, this type of mass analysis is well suited to ionization techniques like MALDI which produces ions in short well-defined pulses. Another consideration is to control velocity spread produced by ions that have variations in their amounts of kinetic energy. The use of longer flight tubes, ion reflectors, or higher accelerating voltages can help minimize the effects of velocity spread. Time-of-flight mass analyzers have a high level of sensitivity and a wider m/z range than quadrupole or ion trap mass analyzers. Also data can be acquired quickly with this type of mass analyzer because no scanning of the mass analyzer is necessary.

Gas chromatography mass spectrometry offers a nice solution for detecting a target in real-time. The gas chromatography (GC) portion of the system separates the chemical mixture into pulses of analyte (e.g., MDF's) and the mass spectrometer (MS) identifies and quantifies the analyte.

Tandem mass spectrometry can utilize combinations of the mass analyzers described above. Tandem mass spectrometers can use a first mass analyzer to separate ions according to their m/z in order to isolate an ion of interest for further analysis. The isolated ion of interest is then broken into fragment ions (called collisionally activated dissociation or collisionally induced dissociation) and the fragment ions are analyzed by the second mass analyzer. These types of tandem mass spectrometer systems are called tandem in space systems because the two mass analyzers are separated in space, usually by a collision cell. Tandem mass spectrometer systems also include tandem in time systems where one mass analyzer is used, however the mass analyzer is used sequentially to isolate an ion, induce fragmentation, and then perform mass analysis.

Mass spectrometers in the tandem in space category have more than one mass analyzer. For example, a tandem quadrupole mass spectrometer system can have a first quadrupole mass filter, followed by a collision cell, followed by a second quadrupole mass filter and then the detector. Another arrangement is to use a quadrupole mass filter for the first mass analyzer and a time-of-flight mass analyzer for the second mass analyzer with a collision cell separating the two mass analyzers. Other tandem systems are known in the art including reflectron-time-of-flight, tandem sector and sector-quadrupole mass spectrometry.

Mass spectrometers in the tandem in time category have one mass analyzer that performs different functions at different times. For example, an ion trap mass spectrometer can be used to trap ions of all m/z. A series of rf scan functions are applied which ejects ions of all m/z from the trap except the m/z of ions of interest. After the m/z of interest has been isolated, an rf pulse is applied to produce collisions with gas molecules in the trap to induce fragmentation of the ions. Then the m/z values of the fragmented ions are measured by the mass analyzer. Ion cyclotron resonance instruments, also known as Fourier transform mass spectrometers, are an example of tandem-in-time systems.

Several types of tandem mass spectrometry experiments can be performed by controlling the ions that are selected in each stage of the experiment. The different types of experiments utilize different modes of operation, sometimes called "scans," of the mass analyzers. In a first example, called a mass spectrum scan, the first mass analyzer and the collision cell transmit all ions for mass analysis into the second mass analyzer. In a second example, called a product ion scan, the ions of interest are mass-selected in the first mass analyzer and then fragmented in the collision cell. The ions formed are then mass analyzed by scanning the second mass analyzer. In a third example, called a precursor ion scan, the first mass analyzer is scanned to sequentially transmit the mass analyzed ions into the collision cell for fragmentation. The second mass analyzer mass-selects the product ion of interest for transmission to the detector. Therefore, the detector signal is the result of all precursor ions that can be fragmented into a common product ion. Other experimental formats include neutral loss scans where a constant mass difference is accounted for in the mass scans. The use of these different tandem mass spectrometry scan procedures can be advantageous when large sets of reporter tags are measured in a single experiment as with multiplex experiments.

In typical applications, the amount of MDF generated by the during the reaction is determined based on cycle threshold (Ct) value, which represents the number of cycles required to generate a detectable amount of nucleic acid. Determination of Ct values is well known in the art. Briefly, during PCR, as the amount of formed amplicon increases, the signal intensity increases to a measurable level and reaches a plateau in later cycles when the reaction enters into a non-logarithmic phase. By plotting signal intensity versus the cycle number during the logarithmic phase of the reaction, the specific cycle at which a measurable signal is obtained can be deduced and used to calculate the quantity of the target before the start of the PCR. Exemplary methods of determining Ct are described in, e.g., Heid et al. Genome Methods 6:986-94, 1996, with reference to hydrolysis probes.

EXAMPLES

Example 1

Evaluation of Exonuclease-Resistant Modification

Figure 2A:
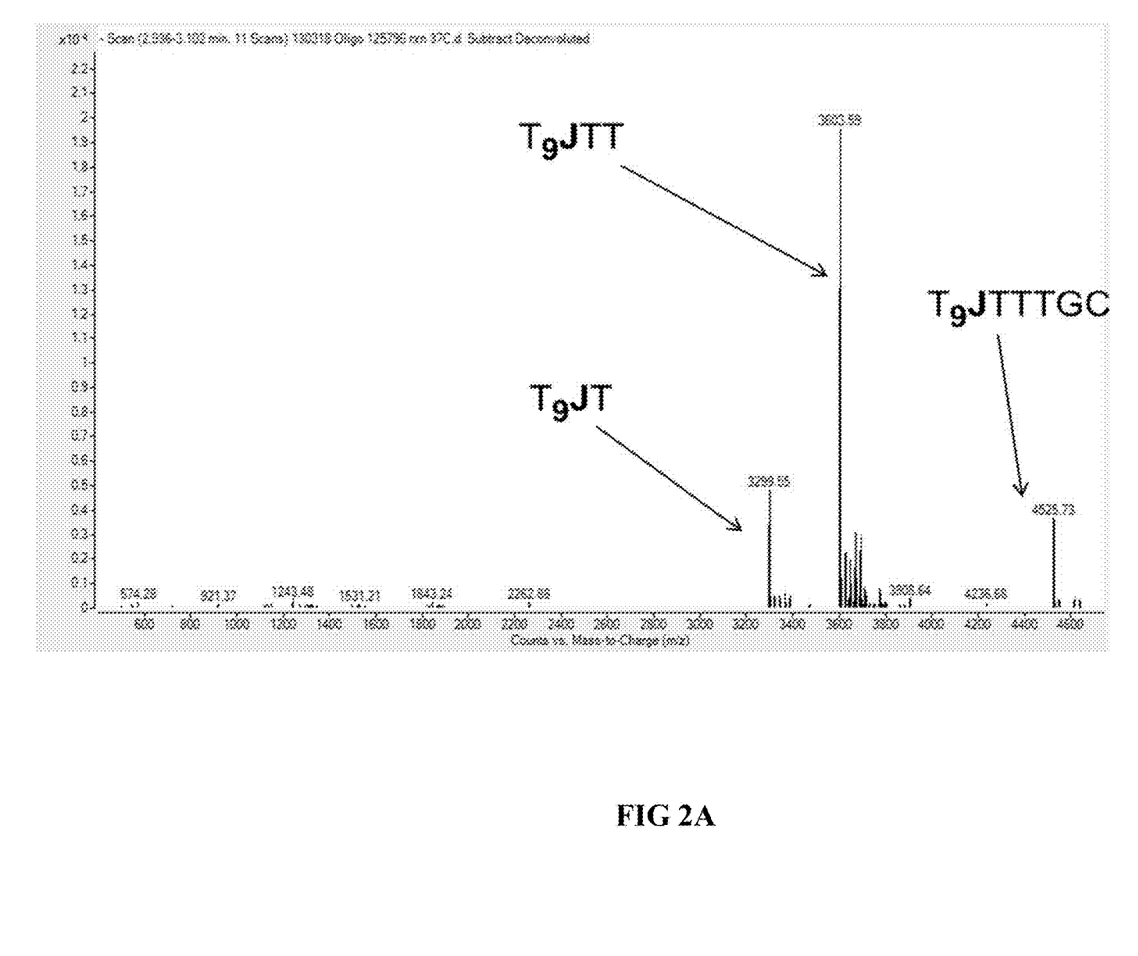
FIG. 2 represents a mass spectrogram which shows the oligonucleotide fragments $T_9JTT$ (SEQ ID NO: 5) and $T_9JT$ (SEQ ID NO: 6) following Exonuclease I digestion of the oligonucleotide $T_9JTTTGC$ (SEQ ID NO: 1), in which J is 2'-O-methyl-uridine (A), HEG spacer (B) or propanediol spacer (C).
Figure 2B:
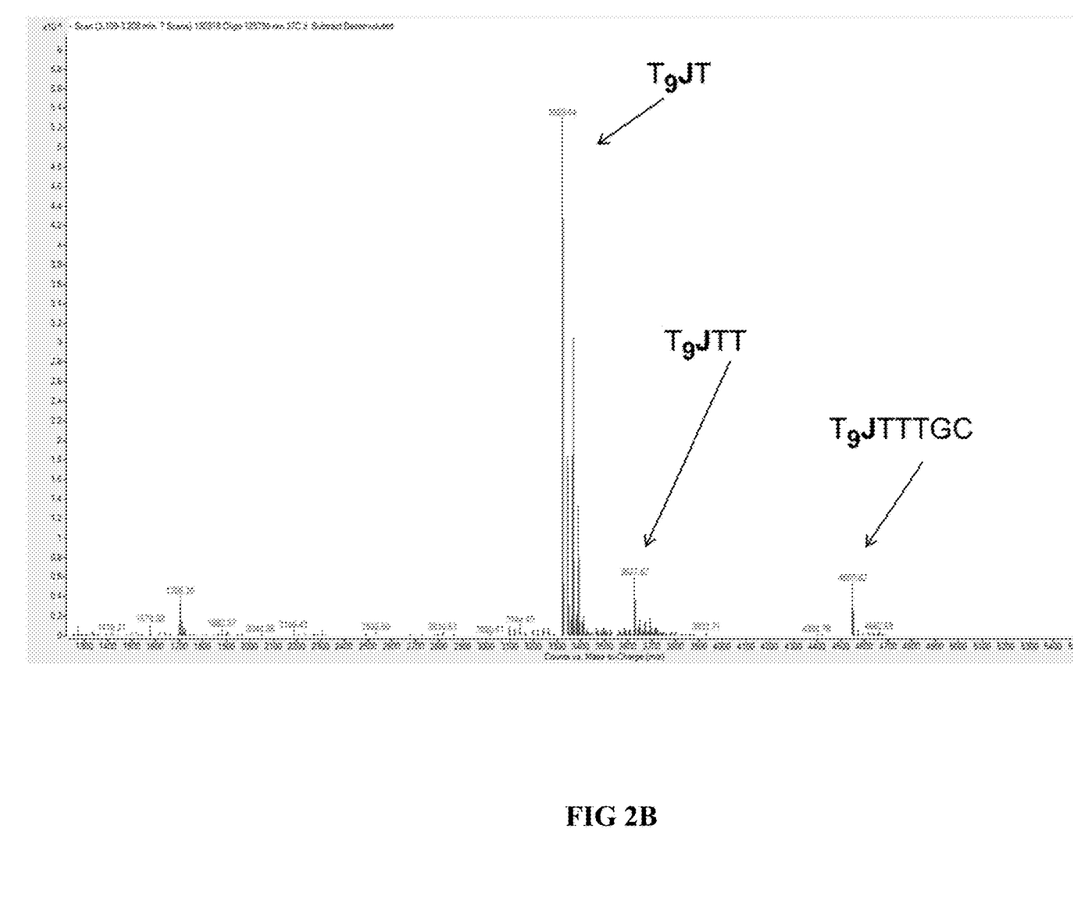
Figure 2C:
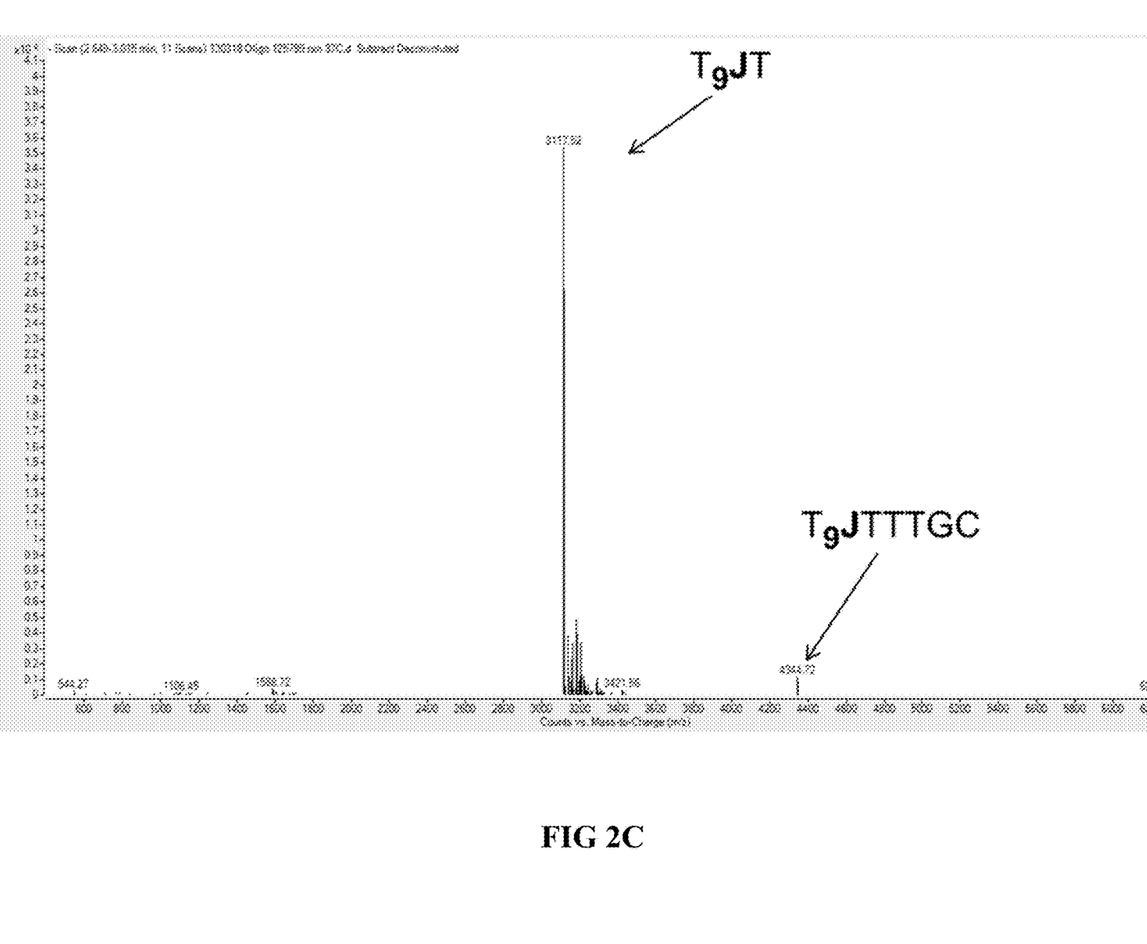

In order to evaluate the different exonuclease-resistant modifications that can be used to practice the methods of the present invention, the following oligonucleotide was synthesized: T9JTTTGC (SEQ ID NO: 1), in which T9 represents the 5' flap portion and J represents the modification. The modifications used in one particular experiment included phosphorothioate, 2'-amino-uridine, 2'-fluoro-uridine, 2'-O-methyl-uridine, a propane-diol spacer, and a HEG (full-name) spacer. 1 µM of each oligonucleotide was suspended in 1× Exonuclease I Buffer (New England Biolabs) and 2 units of Exonuclease I (New England Biolabs) and incubated at 37° C. for thirty minutes. The reactions were terminated by chilling on ice and the exonuclease-digested products were analyzed by liquid chromatography-mass spectrometry (LC-MS) in an Agilent Q-TOF 6530 instrument. The Exonuclease I-digested products from oligonucleotides that contain three of the modifications, 2'-O-methyl-uridine, HEG spacer, and propanediol spacer are shown on the mass spectrograms in FIG. 2 A-C. These results show that these modifications are effective in blocking the digestion of the oligonucleotide beyond the point of attachment of the modification.

Example 2

Detection of EGFR T790M Amplification Using 5'-Flap Probe

A PCR assay was performed to detect the T790M mutation (nucleotide change 2369 C→T) of the human Epidermal Growth Factor Receptor (EGFR) gene. The following primers were used for amplification of a region of the EGFR gene that includes the position of the T790M mutation:

```
                                              (SEQ ID NO: 2)
Forward primer:  5' CCTCCCTCCAGGAAGCCTACGTGA 3'

(E = t-butyl benzyl-dC, SEQ ID NO: 3)
Reverse primer:  5' CAGTCGAAGGGCATGAGCTGEA 3'
```

For detection, the following 5'-Flap Probe was utilized, 5'-$C_6$ECCTGCACGGTGGAGGTGAGGCAGP-3' (SEQ ID NO: 4), where $C_6$ represents the non-complementary 5' Flap portion, E represents 1,3-Propanediol and P represents phosphate. PCR reaction mixtures were prepared on a 96-well plate with the following final concentrations: 50 mM Tris-HCl (pH 8.0), 80-100 mM potassium chloride, 200 µM each dATP, dCTP and dGTP, 400 µM dUTP, 200 nM of each primer, 200 nM 5'-Flap probe, target DNA (1,000-100,000 copies of EGFR plasmid, 20 nM DNA polymerase (with 5' nuclease activity), 0.1 mM EDTA, 2.5 mM magnesium acetate. Amplification and analysis was done using the Roche LightCycler® 480 instrument (Roche Applied Science, Indianapolis, Ind.) The following temperature profile was used: 95° C. for 1 minute (or 2 cycles of 95° C. (10 seconds) to 62° C. (25 seconds) followed by cycling from 92° C. (10 seconds) to 62° C. (25-30 seconds) 99 times. At the conclusion of the PCR reaction, 10 units of Exonuclease I (New England Biolabs) were added to some of the sample wells and the solution was incubated at 37° C. for 30 minutes, followed by chilling on ice.

Figure 3:
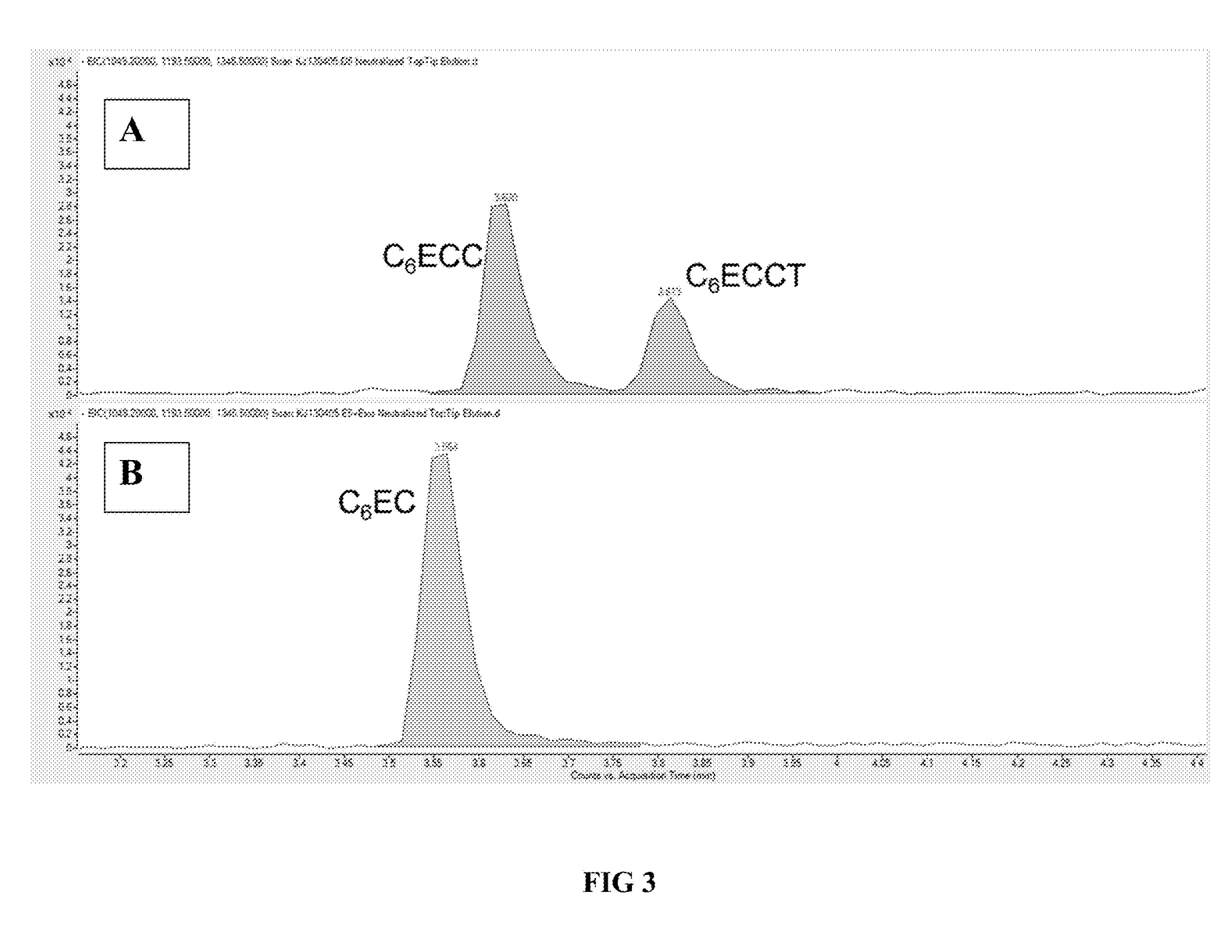
FIG. 3 represents the extracted ion chromatogram (EIC) after LC-MS of the fragments of an EGFR T790M mutant 5'-Flap probe in a PCR amplification reaction and followed without (A) or with (B) subsequent digestion by Exonuclease I.

The reaction products were passed through TopTip (Glygen Corp) anion exchange spin columns for the removal of detergent and other contaminants and then loaded onto the Agilent Q-TOF 6530 instrument and the fragments analyzed by LC-MS. FIG. 3 shows the extracted ion chromatogram (EIC) of the fragments of the 5'-Flap probe prior to (A) and following (B) digestion by Exonuclease I. Two distinct peaks were observed in the reaction without Exonuclease I digestion with the expected masses that correspond to probe fragments with the sequences $C_6$ECC and $C_6$ECCT. However, following Exonuclease I digestion, only a single distinct peak with a mass that corresponds to the probe fragment $C_6$EC was observed and the peaks that correspond to the $C_6$ECC and $C_6$ECCT were no longer observed.

The invention claimed is:

1. A method of detecting the presence or absence of a target nucleic acid sequence in a sample, comprising the steps of:

(a) preparing a reaction mixture by contacting the sample comprising a target nucleic acid with (i) a pair of oligonucleotide primers, wherein a first oligonucleotide primer comprises a sequence complementary to a region in one strand of the target nucleic acid sequence and primes the synthesis of a first extension product, and wherein a second oligonucleotide primer comprises a sequence complementary to a region in said first extension product and primes the synthesis of a nucleic acid strand complementary to said first extension product, and
(ii) an oligonucleotide probe comprising at least two distinct portions,
a first portion comprised of standard nucleotides with or without nucleotide analogs that comprises a sequence that is at least partially complementary to a region of the target nucleic acid sequence wherein said first portion anneals within the target nucleic acid sequence bounded by said pair of oligonucleotide primers, and wherein said first portion is blocked at the 3' terminus to prohibit extension by a nucleic acid polymerase and to prevent cleavage by a 3' to 5' exonuclease; and a second portion attached to the 5' end of the first portion comprised of either nucleotides or non-nucleotides or both nucleotides and non-nucleotides, and comprises a sequence that is non-complementary to the target nucleic acid sequence, wherein said second portion also comprises an exonuclease-resistant modification selected from propanediol spacer, or hexaethylene glycol (HEG) spacer;
(b) amplifying said target nucleic acid sequence with a nucleic acid polymerase having 5' to 3' nuclease activity under conditions that allows annealing of said pair of oligonucleotide primers and said oligonucleotide probe to the target nucleic acid sequence and synthesis of primer extension products from said pair of oligonucleotide primers while the 5' to 3' nuclease activity of said nucleic acid polymerase is able to cleave and release from the annealed oligonucleotide probe, fragments containing the second portion of the oligonucleotide probe with or without additional nucleotides from the first portion of the oligonucleotide probe;
(c) treating said released fragments containing the second portion of the oligonucleotide probe with a 3' to 5' exonuclease that cleaves said fragments up to the exonuclease-resistant modification thereby producing a single fragment having a unique mass-distinguishable size; and
(d) detecting the presence or absence of the single fragment by mass spectrometry, thereby detecting the presence or absence of the target nucleic acid sequence in the sample;
wherein the 3' to 5' exonuclease is selected from the group consisting of Exonuclease I from *E. coli*, Exonuclease IV from *E. coli*, Exonuclease V from *E. coli*, T4 Exonuclease IV from Phage T4, T4 DNA Polymerase from Phage T4, Exonuclease I from Yeast, DNA polymerase α from *Drosophila*, DNA polymerase γ from *Drosophila*, and Snake venom phosphodiesterase.

2. The method of claim 1, wherein two or more target nucleic acids are detected in a single multiplexed reaction.

3. The method of claim 2, wherein two or more oligonucleotide probes are used to detect the two or more target nucleic acids in the single multiplexed reaction.

4. The method of claim 1, wherein the detecting step (d) is preceded by a step of purifying said reaction mixture for removing contaminants of mass spectrometry from said reaction mixture.

5. The method of claim 1, wherein the detecting step (d) is done by a mass spectrometer, selected from the group consisting of Matrix-Assisted Laser Desorption Ionization-Time of Flight (MALDI-TOF) MS, Tandem MS, Electrospray Ionization-Time of Flight (ESI-TOF), ESI-iontrap, Liquid Chromatography (LC)-MS, Gas Chromatography (GC)-MS and Ion Mobility (IM)-MS.

6. The method of claim 1, wherein the nucleic acid polymerase is a thermostable DNA polymerase.

7. A method of detecting the presence or absence of a target nucleic acid sequence in a sample, comprising the steps of:
(a) preparing a reaction mixture by contacting the sample comprising a target nucleic acid with
(i) a pair of oligonucleotide primers, wherein a first oligonucleotide primer comprises a sequence complementary to a region in one strand of the target nucleic acid sequence and primes the synthesis of a first extension product, and wherein a second oligonucleotide primer comprises a sequence complementary to a region in said first extension product and primes the synthesis of a nucleic acid strand complementary to said first extension product, and
(ii) an oligonucleotide probe comprising at least two distinct portions,
a first portion comprised of standard nucleotides with or without nucleotide analogs that comprises a sequence that is at least partially complementary to a region of the target nucleic acid sequence wherein said first portion anneals within the target nucleic acid sequence bounded by said pair of oligonucleotide primers, wherein the first portion also comprises a modification at the 5'-end that renders it resistant to cleavage by a single strand-specific 5'-3'-exonuclease, and a second portion attached to the 3' end of the first portion comprised of either nucleotides or non-nucleotides or both nucleotides and non-nucleotides, and comprises a sequence that is non-complementary to the target nucleic acid sequence, wherein said second portion also comprises a modification selected from propanediol spacer, or hexaethylene glycol (HEG) spacer that renders it resistant to cleavage by the single strand-specific 5'-3' exonuclease;
(b) amplifying said target nucleic acid sequence with a nucleic acid polymerase having 5' to 3' nuclease activity under conditions that allows annealing of said pair of oligonucleotide primers and said oligonucleotide probe to the target nucleic acid sequence and synthesis of primer extension products from said pair of oligonucleotide primers while the 5' to 3' nuclease activity of said nucleic acid polymerase is able to cleave and release from the annealed oligonucleotide probe, fragments containing the second portion of the oligonucleotide probe with or without additional nucleotides from the first portion of the oligonucleotide probe;
(c) treating said released fragments containing the second portion of the oligonucleotide probe with the single strand-specific 5'-3' exonuclease that cleaves said fragments up to the exonuclease-resistant modification thereby producing a single fragment having a unique mass-distinguishable size; and
(d) detecting the presence or absence of the single fragment by mass spectrometry, thereby detecting the presence or absence of the target nucleic acid sequence in the sample;
wherein the single strand-specific 5'-3' exonuclease is selected from the group consisting of Exonuclease from *B. subtilis*, Exonuclease II from yeast, Exonuclease V from yeast, and Exonuclease from *Neurospora crassa*.

8. The method of claim 7, wherein two or more target nucleic acids are detected in a single multiplexed reaction.

9. The method of claim 8, wherein two or more oligonucleotide probes are used to detect the two or more target nucleic acids in the single multiplexed reaction.

10. The method of claim 7, wherein the detecting step (d) is preceded by a step of purifying said reaction mixture for removing contaminants of mass spectrometry from said reaction mixture.

11. The method of claim 7, wherein the detecting step (d) is done by a mass spectrometer, selected from the group consisting of Matrix-Assisted Laser Desorption Ionization-Time of Flight (MALDI-TOF) MS, Tandem MS, Electrospray Ionization-Time of Flight (ESI-TOF), ESI-iontrap, Liquid Chromatography (LC)-MS, Gas Chromatography (GC)-MS and Ion Mobility (IM)-MS.

12. The method of claim 7, wherein the nucleic acid polymerase is a thermostable DNA polymerase.

* * * * *